(12) United States Patent
Dalziel et al.

(10) Patent No.: US 7,622,587 B2
(45) Date of Patent: Nov. 24, 2009

(54) CRYSTALLINE FORM OF A BENZIMIDAZOLE-CARBOXAMIDE MEDICINAL COMPOUND

(75) Inventors: Sean M. Dalziel, San Francisco, CA (US); Kirsten M. Phizackerley, San Rafael, CA (US)

(73) Assignee: Theravance, Inc., South San Francisco, CA (US)

( * ) Notice: Subject to any disclaimer, the term of this patent is extended or adjusted under 35 U.S.C. 154(b) by 29 days.

(21) Appl. No.: 11/807,664

(22) Filed: May 30, 2007

(65) Prior Publication Data

US 2007/0244157 A1    Oct. 18, 2007

Related U.S. Application Data

(62) Division of application No. 11/439,669, filed on May 24, 2006, now Pat. No. 7,256,394.

(60) Provisional application No. 60/684,478, filed on May 25, 2005.

(51) Int. Cl.
*C07D 401/00* (2006.01)

(52) U.S. Cl. ...................................... 546/187

(58) Field of Classification Search ................... 546/187
See application file for complete search history.

(56) References Cited

U.S. PATENT DOCUMENTS

| 6,294,555 | B1 | 9/2001 | Kato et al. |
| 6,696,468 | B2 | 2/2004 | Kato et al. |
| 2006/0270652 | A1 | 11/2006 | McKinnell et al. |

FOREIGN PATENT DOCUMENTS

| ES | 2 154 605 A1 | 4/2001 |
| JP | 11001472 A2 | 1/1999 |
| JP | 20001122784 A2 | 5/2001 |
| JP | 2004277318 A2 | 10/2004 |
| JP | 2004277319 A2 | 10/2004 |
| JP | 2004277320 A2 | 10/2004 |
| WO | WO 97/35860 A1 | 10/1997 |

OTHER PUBLICATIONS

Lopez-Rodriguez et al., "3-D-QSAR/CoMFA and Recognition Models of Benzimidazole Derivatives at the 5-$HT_4$ Receptor", Bioorganic & Medicinal Chemistry Letters, 11, pp. 2807-2811(2001).
Lopez-Rodriguez et al., "Benzimidazole Derivates. Part 1: Synthesis and Structure-Activity Relationships of New Benzimidazole-4-carboxamides and Carboxylates as Potent and Selective 5-$HT_4$ Receptor Antagonists", Bioorganic & Medicinal Chemistry, 7, pp. 2271-2281 (1999).
Lopez-Rodriguez et al., "Benzimidazole Derivatives. 3. 3D-QSAR/CoMFA Model and Computational Simulation for the Recognition of 5-$HT_4$ Receptor Antagonists", J. Med. Chem., 45, pp. 4806-4815 (2000).
Lopez-Rodriguez et al., "Benzimidazone derivatives 4. The recognition of the voluminous substituent attached to the basic amino group of 5-$HT_4$ receptor antagonists", Journal of Computer-Aided Molecular Design, 17, pp. 515-524 (2003).
Lopez-Rodriguez et al., "Design and Synthesis of New Benzimidazole-Arylpiperazine Derivatives Acting as Mixed 5-$HT_{1A}$/5-$HT_3$ Ligands", Bioorganic & Medicinal Chemistry Letters, 13, pp. 3177-3180 (2003).
Lopez-Rodriguez et al., "Study of the bioactive conformation of novel 5-$HT_4$ receptor ligands: influence of an intramolecular hydrogen bond", Tetrahedron, 57, pp. 6745-6749 (2001).
Harada et al., "Novel *N*-[1-(1-Substituted 4-Piperidinylmethyl)-4-piperidinyl]benzamides as Potent Colonic Prokinetic Agents", Bioorganic & Medicinal Chemistry Letters 12, pp. 967-970 (2002).

*Primary Examiner*—D. Margaret Seaman
*Assistant Examiner*—Nizal S Chandrakumar
(74) *Attorney, Agent, or Firm*—Jeffrey A. Hagenah; Roberta P. Saxon

(57) ABSTRACT

The invention provides crystalline forms of the novel benzimidazole-carboxamide 5-$HT_4$ receptor agonist compound, 4-(4-{[(2-isopropyl-1H-benzoimidazole-4-carbonyl)amino]methyl}-piperidin-1-ylmethyl)piperidine-1-carboxylic acid methyl ester. The invention also provides pharmaceutical compositions comprising the crystalline compound, methods of using the compound to treat diseases associated with 5-$HT_4$ receptor activity, and processes useful for preparing crystalline forms of the compound.

18 Claims, 3 Drawing Sheets

CRYSTALLINE FORM OF A BENZIMIDAZOLE-CARBOXAMIDE MEDICINAL COMPOUND

CROSS REFERENCE TO RELATED APPLICATIONS

This application is a divisional of U.S. application Ser. No. 11/439,669, filed May 24, 2006, now U.S. Pat. No. 7,256,294 B2, which claims the benefit of U.S. Provisional Application No. 60/684,478, filed on May 25, 2005, the disclosures of which are incorporated herein by reference in their entirety.

BACKGROUND OF THE INVENTION

1. Field of the Invention

The invention is directed to crystalline forms of a benzimidazole-carboxamide compound which is useful as a 5-$HT_4$ receptor agonist. The invention is also directed to pharmaceutical compositions comprising the crystalline compound, methods of using the compound for treating or preventing medical conditions mediated by 5-$HT_4$ receptor activity, and processes useful for preparing the compound in crystalline form.

2. State of the Art

Serotonin (5-hydroxytryptamine, 5-HT) is a neurotransmitter that is widely distributed throughout the body, both in the central nervous system and in peripheral systems. At least seven subtypes of serotonin receptors have been identified and the interaction of serotonin with these different receptors is linked to a wide variety of physiological functions. There has been, therefore, substantial interest in developing therapeutic agents that target specific 5-HT receptor subtypes.

In particular, characterization of 5-$HT_4$ receptors and identification of pharmaceutical agents that interact with them has been the focus of significant recent activity. (See, for example, the review by Langlois and Fischmeister, *J. Med. Chem.* 2003, 46, 319-344.) 5-$HT_4$ receptor agonists are useful for the treatment of disorders of reduced motility of the gastrointestinal tract. Such disorders include irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

Despite the broad utility of pharmaceutical agents modulating 5-$HT_4$ receptor activity, few 5-$HT_4$ receptor agonist compounds are in clinical use at present. Accordingly, there is a need for new 5-$HT_4$ receptor agonists that achieve their desired effects with minimal side effects. Preferred agents may possess, among other properties, improved selectivity, potency, pharmacokinetic properties, and/or duration of action.

To effectively use such agents, it is desirable that the 5-$HT_4$ receptor agonist compounds be provided in a crystalline form that can be readily manufactured and that has acceptable physical and chemical stability.

SUMMARY OF THE INVENTION

The invention provides crystalline forms of a novel compound that possesses 5-$HT_4$ receptor agonist activity. Among other properties, the compound of the invention has been found to be a potent and selective 5-$HT_4$ receptor agonist. In addition, the compound of the invention has been found to exhibit favorable pharmacokinetic properties which are predictive of good bioavailability upon oral administration.

Accordingly, the invention provides crystalline forms of the compound having the chemical structure:

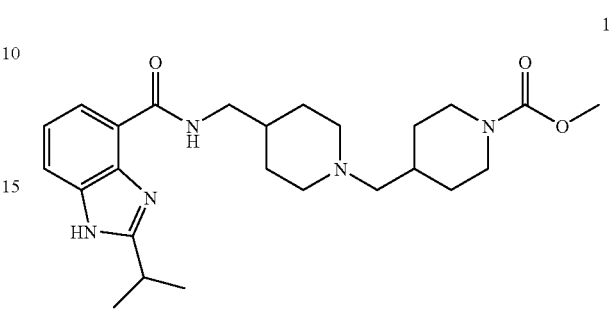

or a solvate thereof. The above compound (hereinafter compound 1) is designated 4-(4-{[(2-isopropyl-1H-benzoimidazole-4-carbonyl)amino]methyl}-piperidin-1-ylmethyl)piperidine-1-carboxylic acid methyl ester, according to the AutoNom software, provided by MDL Information Systems, GmbH (Frankfurt, Germany). The fused ring structure "benzoimidazole" is alternatively named "benzimidazole". The two terms are equivalent as used herein.

A crystalline form of 4-(4-{[(2-isopropyl-1H-benzoimidazole-4-carbonyl)amino]methyl}-piperidin-1-ylmethyl)piperidine-1-carboxylic acid methyl ester has been found to have a melting temperature in the range of about 145° C. to about 155° C., typically between about 146 and about 148° C., a degradation temperature above about 240° C., and to exhibit weight changes of less than about 0.25% when exposed to a range of relative humidity between about 2% and about 90% at room temperature. Additional crystalline forms of 4-(4-{[(2-isopropyl-1H-benzoimidazole-4-carbonyl)amino]methyl}-piperidin-1-ylmethyl)piperidine-1-carboxylic acid methyl ester are also provided in further aspects of the invention.

Among other uses, the crystalline forms of compound 1 are expected to be useful for preparing pharmaceutical compositions for treating disorders of reduced motility of the gastrointestinal tract. Accordingly, in another of its composition aspects, the invention provides a pharmaceutical composition comprising a pharmaceutically-acceptable carrier and crystalline 4-(4-{[(2-isopropyl-1H-benzoimidazole-4-carbonyl)amino]methyl}-piperidin-1-ylmethyl)piperidine-1-carboxylic acid methyl ester or a solvate thereof.

In addition, the invention provides a method of treating a disease or condition associated with 5-$HT_4$ receptor activity, e.g. a disorder of reduced motility of the gastrointestinal tract, the method comprising administering to the mammal, a therapeutically effective amount of the crystalline compound of the invention.

In another method aspect, the invention provides processes for preparing compound 1 in crystalline form.

The invention also provides the crystalline compound of the invention as described herein for use in medical therapy, as well as the use of the crystalline compound of the invention in the manufacture of a formulation or medicament, especially for the manufacture of a medicament for treating a disorder of reduced motility of the gastrointestinal tract in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
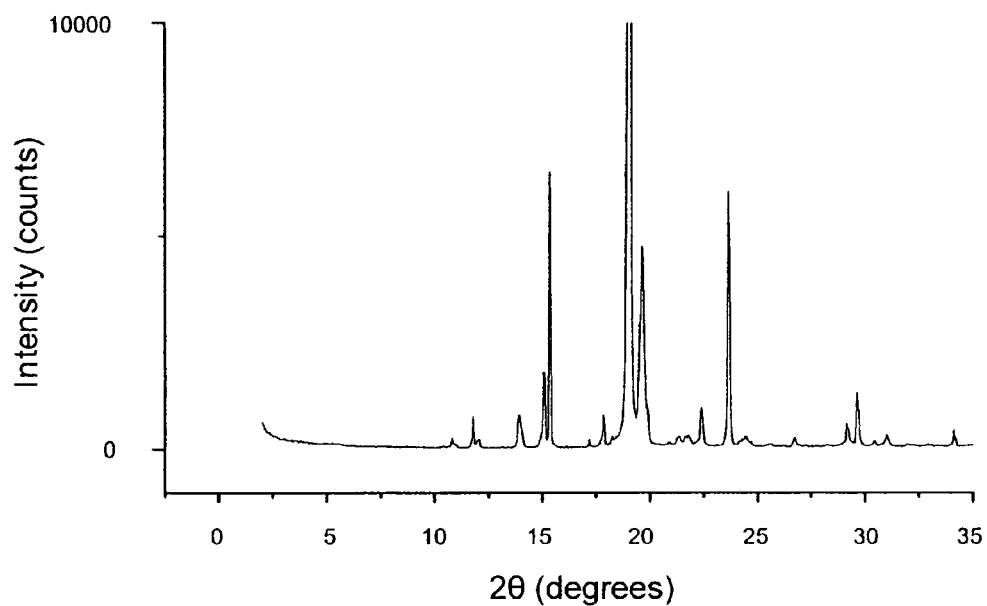
FIG. 1 shows a powder x-ray diffraction (PXRD) pattern of crystalline 4-(4-{[(2-isopropyl-1H-benzoimidazole-4-carbonyl)amino]methyl}-piperidin-1-ylmethyl)piperidine-1-carboxylic acid methyl ester (Form I).

The invention provides crystalline forms of a novel benzimidazole-carboxamide 5-HT$_4$ receptor agonist.

Definitions

When describing the compound, compositions and methods of the invention, the following terms have the following meanings, unless otherwise indicated.

The term "compound" means a compound that was synthetically prepared or produced in any other way, such as by metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, hydrobromic, hydrochloric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), naphthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

The term "amino-protecting group" means a protecting group suitable for preventing undesired reactions at an amino nitrogen. Representative amino-protecting groups include, but are not limited to, formyl; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

Synthetic Procedures

Compound 1, 4-(4-{[(2-isopropyl-1H-benzoimidazole-4-carbonyl)amino]methyl}-piperidin-1-ylmethyl)piperidine-1-carboxylic acid methyl ester, can be prepared from readily available starting materials using the following general procedure. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

The compound of the invention may be prepared by reacting a piperidinylmethyl-carboxylic acid amide intermediate (II):

(II)

[Structure of compound II: benzimidazole-isopropyl with carboxamide linked to piperidinylmethyl (NH piperidine)]

with formylpiperidinyl intermediate (III):

(III)

[Structure: 4-formylpiperidine-1-carboxylic acid methyl ester]

The reaction is typically conducted by contacting (II) with between about 1 and about 2 equivalents of intermediate (III) in an inert diluent in the presence of between about 1 and about 2 equivalents of a reducing agent. Optionally, about one equivalent of a weak acid, such as acetic acid can be included to accelerate the reaction. The reaction may be conducted at a temperature between about 0° C. and about 30° C., typically between about 20° C. and about 30° C., for about 0.25 to about 2 hours, or until the reaction is substantially complete. The product is isolated by standard procedures.

Suitable inert diluents include dichloromethane, N,N-dimethylformamide trichloromethane, 1,1,2,2-tetrachloroethane, and the like. Typical reducing agents include sodium triacetoxyborohydride, sodium borohydride, and sodium cyanoborohydride. When the amine (II) is supplied as an acid salt, typically between about 1 and about 3 equivalents of an amine base, such as N,N-diisopropylethylamine, triethylamine, pyridine, and the like, is included in the reaction.

The piperidinylmethyl-carboxylic acid amide intermediate (II) is prepared from readily available starting materials by the procedure illustrated in Scheme A.

(V)

[Structure of compound V: protected version with $P^1$ group]

(II)

[Structure of compound II]

where $P^1$ represents an amino protecting group, such as tert-butoxycarbonyl (Boc).

First, the carboxylic acid (IV) is reacted with a protected aminomethyl piperidine to form a protected intermediate (V). This reaction is typically conducted by contacting (IV) with between about 1 and about 2 equivalents of protected aminomethylpiperidine in a polar aprotic diluent, in the presence of an amide coupling agent, for example N-ethyl-N'-(3-dimethylaminopropyl)carbodiimide hydrochloride (EDC) combined with hydroxybenzotriazole (HOBt) or 1,1'-carbonyldiimidazole (CDI) combined with 1,4-diazabicyclo[2,2,2]octane (DABCO). The reaction is typically conducted at a temperature in the range of about 0° C. to about 60° C. for between about 1 and about 24 hours or until the reaction is substantially complete.

The protecting group $P^1$ is removed from intermediate (V) by conventional means to provide intermediate (II). For example, when Boc is used as the protecting group, it may be removed by treatment with an acid, such as trifluoroacetic acid or hydrochloric acid.

The carboxylic acid (IV) can be prepared from a diaminobenzoic acid or ester by the process illustrated in Scheme B:

Scheme B

[Structures: compound (VII) diaminobenzoate reacting with isobutyric acid to give compound (IV)]

(VII) → (IV)

where R represents methyl or hydrogen. Intermediate (VII) is reacted with isobutyric acid to form the acid intermediate Scheme A

[Structures: compound (IV) benzimidazole carboxylic acid + protected aminomethylpiperidine]

(IV)

(IV). This reaction is typically conducted by contacting the acid or ester (VII) with between about 2 and about 4 equivalents of isobutyric acid in an aqueous acidic solution. The reaction is typically conducted at a temperature in the range of about 80° C. to about 100° C. for about 12 to about 72 hours. The pH of the solution is then raised by the addition of base, such as sodium hydroxide, and the product isolated by conventional means.

A convenient process for providing intermediate (VII) as the methyl ester uses 2-amino-3-nitrobenzoic acid methyl ester (VI):

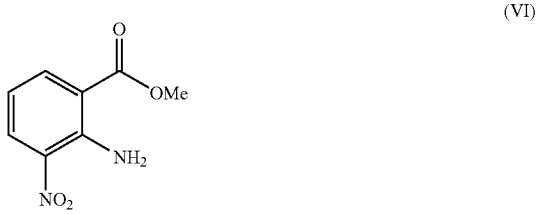

as the starting material. Typically, 2-amino-3-nitrobenzoic acid methyl ester (VI) is dissolved in a polar diluent and reduced by exposure to a hydrogen atmosphere in the presence of a transition metal catalyst to provide the diaminobenzoic acid methyl ester (VII). The reaction is typically conducted at ambient temperature for about 12 to about 72 hours.

A process for preparing the formylpiperidinyl intermediate (III) is illustrated in Scheme C.

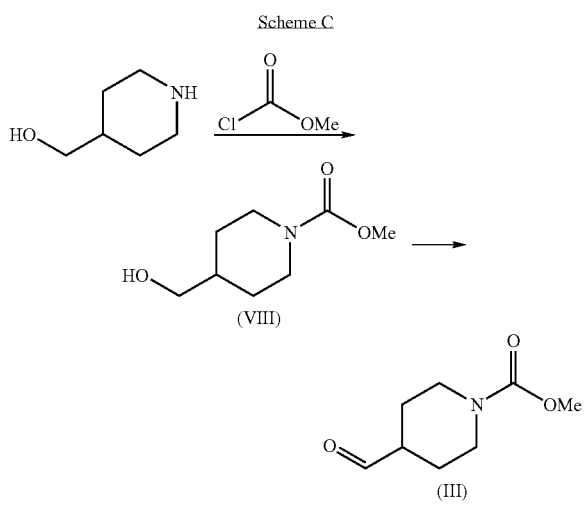

First 4-hydroxymethylpiperidine is reacted with methylchloroformate to form the hydroxymethylpiperidine intermediate (VIII). The reaction is typically conducted by contacting 4-hydroxymethylpiperidine in an aqueous solution with between about 3 and about 5 equivalents of methylchloroformate in the presence of between about 3 and about 5 equivalents of base. The reaction is typically conducted at a temperature in the range of about 0° C. to about 30° C. for about 12 to about 72 hours or until the reaction is substantially complete. Intermediate (VIII) is then oxidized to form the formylpiperidinyl intermediate (III). The oxidation reaction typically makes use of an oxidation reagent such as a combination of oxalyl chloride and dimethylsulfoxide (Swern oxidation), a chromate reagent, such as pyridinium chlorochromate, or an oxidizing agent, such as sodium hypochlorite, together with a catalyst such as 2,2,6,6-tetramethyl-1-piperidinyloxy free radical (TEMPO).

Further details regarding specific reaction conditions and other procedures for preparing compound 1 or intermediates thereto are described in the examples below and in the commonly-assigned U.S. Provisional Application No. 60/684,478, and in U.S. application Ser. No. 11/439,671, filed on even date herewith, which is incorporated herein by reference.

Crystalline Forms

The invention provides 4-(4-{[(2-isopropyl-1H-benzoimidazole-4-carbonyl)amino]methyl}-piperidin-1-ylmethyl)piperidine-1-carboxylic acid methyl ester (compound 1) in crystalline freebase form or a solvate thereof. Three distinguishable forms of crystalline 4-(4-{[(2-isopropyl-1H-benzoimidazole-4-carbonyl)amino]methyl}-piperidin-1-ylmethyl)piperidine-1-carboxylic acid methyl ester have been observed.

Crystalline Form I of the present invention is a crystalline freebase. Form I is characterized by a powder x-ray diffraction (PXRD) pattern having two or more diffraction peaks at 2θ values selected from 15.08±0.20, 15.41±0.20, 19.00±0.20, 19.70±0.20, and 23.68±0.20. In particular, Form I is characterized by a powder x-ray diffraction pattern having diffraction peaks at 2θ values of 19.00±0.20 and 19.70±0.20.

As is well known in the field of powder x-ray diffraction, peak positions of PXRD spectra are relatively less sensitive to experimental details, such as details of sample preparation and instrument geometry, than are the relative peak heights. Thus, in one aspect, the crystalline Form I is characterized by a powder x-ray diffraction pattern in which the peak positions are substantially in accordance with those shown in FIG. 1.

Form I has been further characterized by x-ray diffraction analysis of crystal structure, providing the following lattice parameters: unit cell is orthorhombic with dimensions a=16.9053 Å, b=9.5172 Å, c=15.4659 Å; space group is $Pna2_1$; calculated density is 1.22 g/cm$^3$. The resulting molecular structure confirms the chemical composition is that of compound 1 and that the assymetric unit does not contain water or other solvent molecules. Powder x-ray diffraction peaks predicted from the derived atomic positions are in excellent agreement with observed results.

Figure 2:
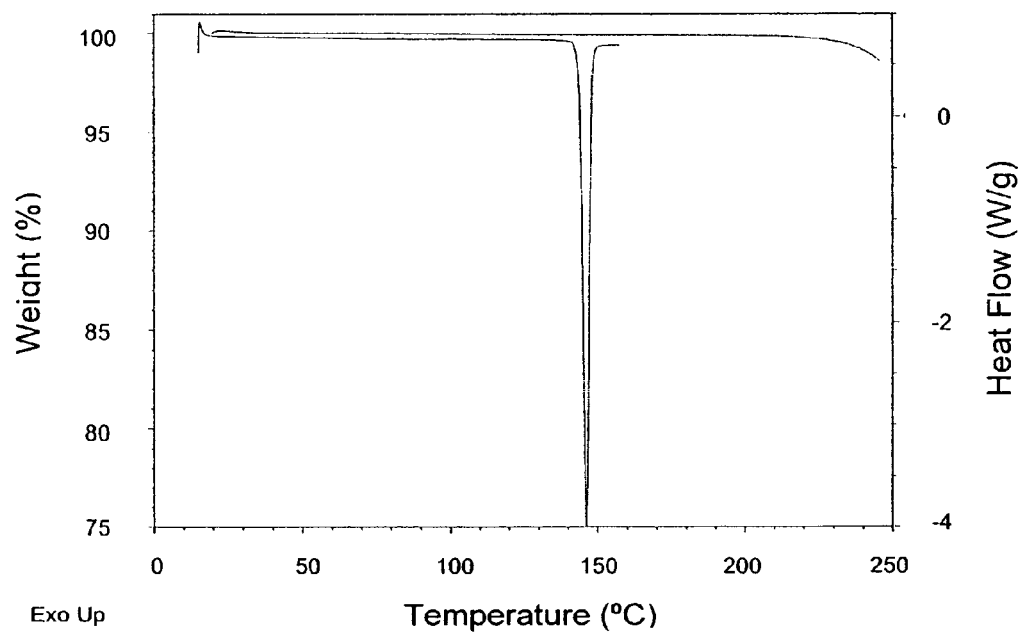
FIG. 2 shows a differential scanning calorimetry (DSC) trace (top trace, right vertical axis) and a thermal gravimetric analysis (TGA) trace (bottom trace, left vertical axis) for crystalline 4-(4-{[(2-isopropyl-1H-benzoimidazole-4-carbonyl)amino]methyl}-piperidin-1-ylmethyl)piperidine-1-carboxylic acid methyl ester (Form I).

Crystalline Form I of the present invention is also characterized by high temperature thermal stability as evidenced by its differential scanning calorimetry (DSC) profile which exhibits a peak in endothermic heat flow in the range of about 145° C. to about 155° C., typically between about 146 and 148° C., as illustrated in FIG. 2, which may be identified as a melting point. Furthermore, the thermal gravimetric analysis (TGA) profile shows no significant weight change event below the onset of degradation which is above about 240° C.

In yet another aspect, the present crystalline form is characterized by its infrared absorption spectrum which shows significant absorption bands at about 766, 1097, 1251, 1413, 1449, 1579, 1609, 1640, and 1696 cm$^{-1}$.

Figure 3:
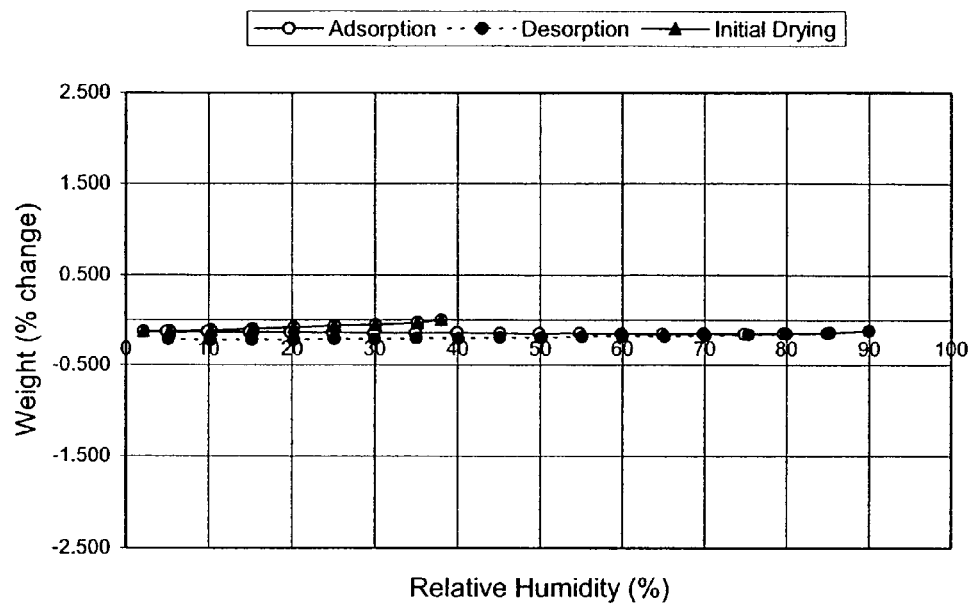
FIG. 3 shows a dynamic moisture sorption (DMS) isotherm for crystalline 4-(4-{[(2-isopropyl-1H-benzoimidazole-4-carbonyl)amino]methyl}-piperidin-1-ylmethyl)piperidine-1-carboxylic acid methyl ester (Form I).

The present crystalline form has been demonstrated to have a reversible sorption/desorption profile with an exceptionally low level of hygroscopicity (i.e., less than about 0.25% weight gain in the humidity range of 2% relative humidity to 90% relative humidity at room temperature) as shown in FIG. 3.

Additionally, crystalline Form I of compound 1 has been found to be stable upon exposure to elevated temperature and humidity. After storage for three months at 40° C. and 75% relative humidity, there were no detectable changes in the DSC, TGA, or PXRD profiles, in the chemical purity as determined by HPLC analysis, and no observable changes in visual appearance. There were also no changes detectable by DSC, TGA, or PXRD after milling particles of Form I from a volume-based mean particle size of about 470 microns to a volume-based mean particle size of about 15, about 22, or about 29 microns.

Figure 4:
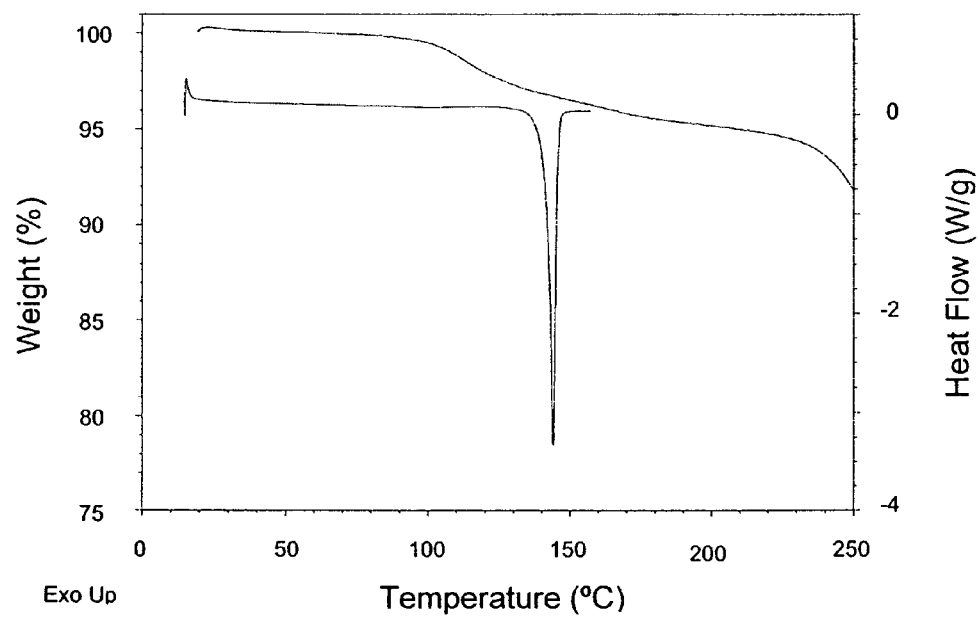
FIG. 4 shows a differential scanning calorimetry (DSC) trace (top trace, right vertical axis) and a thermal gravimetric analysis (TGA) trace (bottom trace, left vertical axis) for crystalline 4-(4-{[(2-isopropyl-1H-benzoimidazole-4-carbonyl)amino]methyl}-piperidin-1-ylmethyl)piperidine-1-carboxylic acid methyl ester (Form II).

Crystalline Form II of compound 1 is characterized by the DSC and TGA profiles of FIG. 4. TGA analysis shows an onset of weight loss in the temperature range of about 95 to about 105° C., typically at about 100° C., in a step profile consistent with water or solvent loss, while the DSC profile exhibits a peak in endothermic heat flow at between about 143 and about 145° C., concurrent with the melting event. The PXRD pattern of Form II is indistinguishable from that of Form I. While positive identification has not been made, the TGA profile of Form II is consistent with the interpretation of Form II as a solvate.

Figure 5:
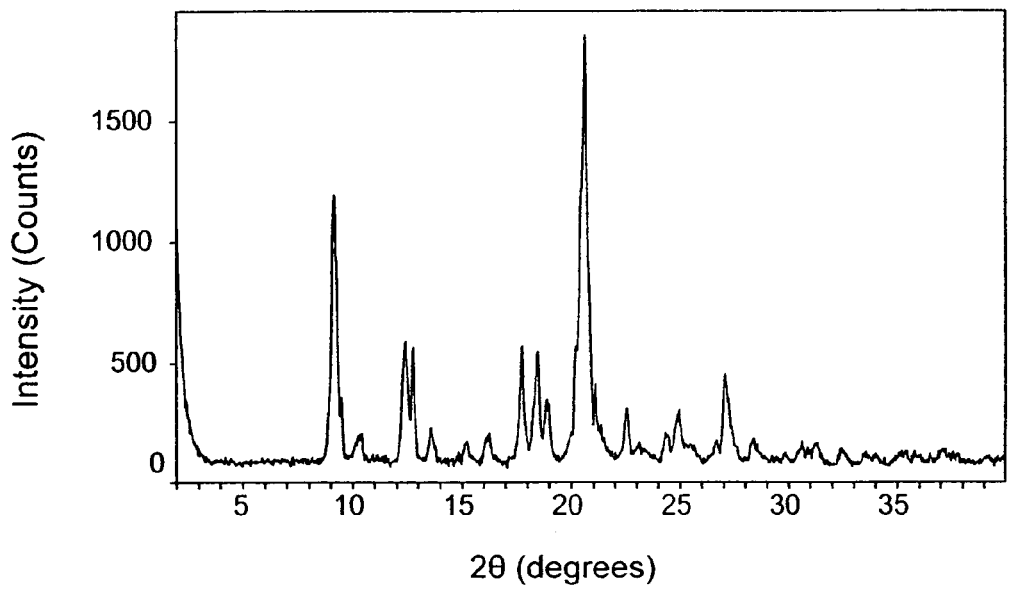
FIG. 5 shows a powder x-ray diffraction (PXRD) pattern of crystalline 4-(4-{[(2-isopropyl-1H-benzoimidazole-4-carbonyl)amino]methyl}-piperidin-1-ylmethyl)piperidine-1-carboxylic acid methyl ester (Form III).

The third crystalline form of the invention has been identified as a monohydrate. Form III is characterized by a powder x-ray diffraction (PXRD) pattern having two or more diffraction peaks at 2θ values selected from 9.14±0.20, 12.41±0.20, 12.74±0.20, 17.75±0.20, 18.47±0.20, 20.63±0.20, 21.13±0.20, and 27.05±0.20, as illustrated in FIG. 5. In particular, Form III is characterized by a powder x-ray diffraction pattern having diffraction peaks at 2θ values of 9.14±0.20, and 20.63±0.20.

Figure 6:
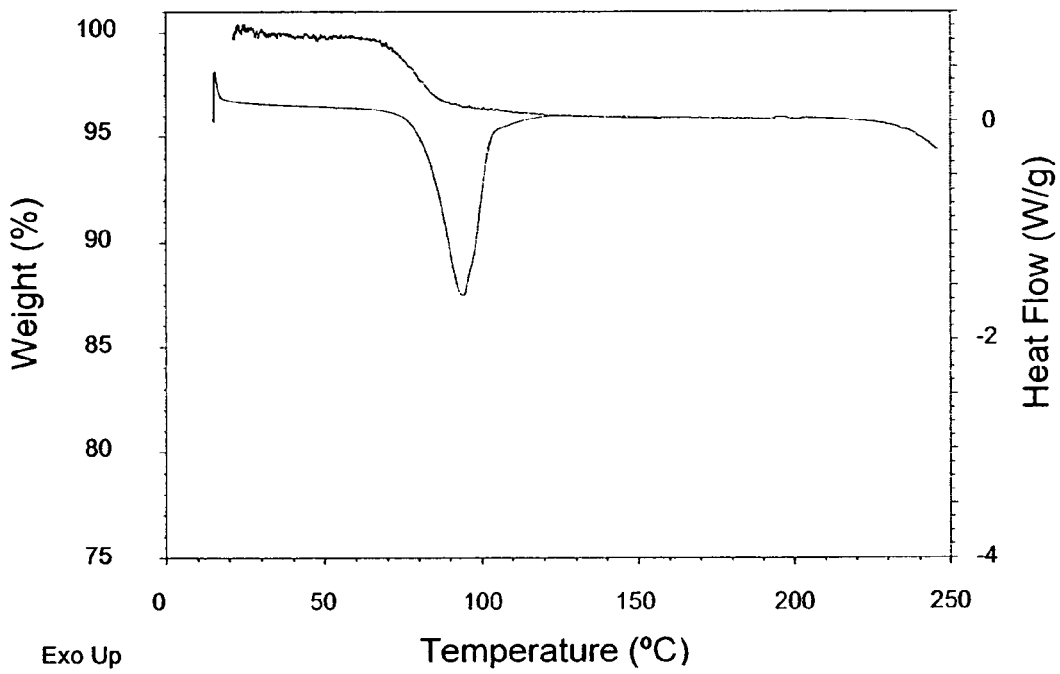
FIG. 6 shows a differential scanning calorimetry (DSC) trace (top trace, right vertical axis) and a thermal gravimetric analysis (TGA) trace (bottom trace, left vertical axis) for crystalline 4-(4-{[(2-isopropyl-1H-benzoimidazole-4-carbonyl)amino]methyl}-piperidin-1-ylmethyl)piperidine-1-carboxylic acid methyl ester (Form m).

The DSC and TGA profiles of Form III, shown in FIG. 6, demonstrate the material undergoes a step profile weight loss with onset in the temperature range of about 65 to about 75° C., typically at about 70° C., and a peak in endothermic heat flow at a temperature between about 90 and about 100° C., consistent with loss of the monohydrate water and subsequent melting. Form III has been further characterized by x-ray diffraction analysis of crystal structure, providing the following lattice parameters: unit cell is monoclinic with dimensions a=14.8101 Å, b=9.9985 Å, c=17.9222 Å; β=106.302°, space group is $P2_1/n$; calculated density is 1.23 g/cm³. The resulting molecular structure confirms the chemical composition is that of compound 1 and that the assymetric unit contains a single water molecule.

The separate crystalline forms of the present invention may be reproducibly obtained by the following procedures. Crystalline Form I may be prepared by dispersing compound 1 in an inert diluent selected from acetonitrile, ether, cyclohexane, and ethyl acetate in a proportion of between about 15 mg and about 25 mg compound 1 per milliliter of diluent to form a mixture, and allowing the mixture to evaporate at ambient temperature, resulting in crystal formation.

Alternatively, Form I may be obtained by a solvent exchange process from crude compound 1 in solution, without first isolating amorphous compound 1, as described in Example 3 below. Typically the reaction to prepare compound 1 is carried out in a polar aprotic diluent, such as dichloromethane, in which the compound is highly soluble. To prepare crystalline Form I, acetonitrile is added while vacuum distilling the crude reaction product to remove the dichloromethane. A mixture having between about 1 and about 200 mg compound 1 per milliliter of acetonitrile, typically between about 50 and about 125 mg compound 1 per milliliter of acetonitrile, is prepared from the residue remaining after distillation and heated to a temperature sufficient to dissolve the residue, for example a temperature of about 75° C. The mixture is then cooled to a temperature of no more than about 20° C. to provide crystalline Form I, which is isolated by conventional procedures. In an exemplary process, the mixture is cooled until nucleation occurs, typically at a temperature of between about 55 and about 65° C. and held at that temperature for about an hour. It is then cooled at a rate of between about 0.25 and about 0.4° C. per minute to a temperature of about 20° C. To increase the yield of crystalline Form I, the mixture may be further cooled at a rate of between about 0.5 and about 0.75° C. per minute to a temperature of between about 0 and about 5° C.

To prepare Form II, amorphous compound 1 is dispersed in hexane at ambient temperature to a final concentration of about 10 mg/mL and the resulting mixture is sonicated. After about 24 hours at ambient temperature, crystalline solids of Form II are obtained. Form III is prepared by dissolving amorphous amorphous compound 1 in a 1:1 ethanol:water solvent mixture at ambient temperature to a final concentration of about 20 mg/mL and sonicating the solution for about 30 seconds. The solution is allowed to partially evaporate in an uncapped vial. After about 24 hours, crystalline solids of Form III are obtained.

Pharmaceutical Compositions

The crystalline benzimidazole-carboxamide compound of the invention is typically administered to a patient in the form of a pharmaceutical composition. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a crystalline form of compound 1. Optionally, such pharmaceutical compositions may contain other therapeutic and/or formulating agents if desired.

The pharmaceutical compositions of the invention typically contain a therapeutically effective amount of the compound of the present invention. Typically, such pharmaceutical compositions will contain from about 0.1 to about 95% by weight of the active agent. i.e. the present compound; including, from about 5 to about 70% by weight; and from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially-available from, for example, Sigma, P.O. Box 14508, St. Louis, Mo. 63178. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, such as microcrystalline cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions.

The pharmaceutical compositions of the invention are typically prepared by thoroughly and intimately mixing or blending a compound of the invention with a pharmaceutically-acceptable carrier and one or more optional ingredients. If necessary or desired, the resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like.

In a preferred embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise a compound of the present invention as the active ingredient and one or more pharmaceutically-acceptable carriers, such as sodium citrate or dicalcium phosphate. Optionally or alternatively, such solid dosage forms may also comprise: (1) fillers or extenders, such as starches, microcrystalline cellulose, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the present invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the present invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas.

Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compound of the invention can also be administered transdermally using known transdermal delivery systems and excipients. For example, the compound of the invention can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following formulations illustrate representative pharmaceutical compositions of the present invention where compound of the invention means a crystalline form of compound 1:

FORMULATION EXAMPLE A

Hard gelatin capsules for oral administration are prepared as follows:

| Ingredients | Amount |
| --- | --- |
| Compound of the invention | 50 mg |
| Lactose (spray-dried) | 200 mg |
| Magnesium stearate | 10 mg |

Representative Procedure: The ingredients are thoroughly blended and then loaded into a hard gelatin capsule (260 mg of composition per capsule).

FORMULATION EXAMPLE B

Hard gelatin capsules for oral administration are prepared as follows:

| Ingredients | Amount |
| --- | --- |
| Compound of the invention | 20 mg |
| Starch | 89 mg |
| Microcrystalline cellulose | 89 mg |
| Magnesium stearate | 2 mg |

Representative Procedure: The ingredients are thoroughly blended and then passed through a No. 45 mesh U.S. sieve and loaded into a hard gelatin capsule (200 mg of composition per capsule).

FORMULATION EXAMPLE C

Capsules for oral administration are prepared as follows:

| Ingredients | Amount |
| --- | --- |
| Compound of the invention | 10 mg |
| Polyoxyethylene sorbitan monooleate | 50 mg |
| Starch powder | 250 mg |

Representative Procedure: The ingredients are thoroughly blended and then loaded into a gelatin capsule (310 mg of composition per capsule).

FORMULATION EXAMPLE D

Tablets for oral administration are prepared as follows:

| Ingredients | Amount |
| --- | --- |
| Compound of the invention | 5 mg |
| Starch | 50 mg |
| Microcrystalline cellulose | 35 mg |
| Polyvinylpyrrolidone (10 wt. % in water) | 4 mg |
| Sodium carboxymethyl starch | 4.5 mg |
| Magnesium stearate | 0.5 mg |
| Talc | 1 mg |

Representative Procedure: The active ingredient, starch and cellulose are passed through a No. 45 mesh U.S. sieve and mixed thoroughly. The solution of polyvinylpyrrolidone is mixed with the resulting powders, and this mixture is then passed through a No. 14 mesh U.S. sieve. The granules so produced are dried at 50-60° C. and passed through a No. 18 mesh U.S. sieve. The sodium carboxymethyl starch, magnesium stearate and talc (previously passed through a No. 60 mesh U.S. sieve) are then added to the granules. After mixing, the mixture is compressed on a tablet machine to afford a tablet weighing 100 mg.

FORMULATION EXAMPLE E

Tablets for oral administration are prepared as follows:

| Ingredients | Amount |
| --- | --- |
| Compound of the invention | 25 mg |
| Microcrystalline cellulose | 400 mg |
| Silicon dioxide fumed | 10 mg |
| Stearic acid | 5 mg |

Representative Procedure: The ingredients are thoroughly blended and then compressed to form tablets (440 mg of composition per tablet).

FORMULATION EXAMPLE F

Single-scored tablets for oral administration are prepared as follows:

| Ingredients | Amount |
| --- | --- |
| Compound of the invention | 15 mg |
| Cornstarch | 50 mg |
| Croscarmellose sodium | 25 mg |
| Lactose | 120 mg |
| Magnesium stearate | 5 mg |

Representative Procedure: The ingredients are thoroughly blended and compressed to form a single-scored tablet (215 mg of compositions per tablet).

FORMULATION EXAMPLE G

A suspension for oral administration is prepared as follows:

| Ingredients | Amount |
|---|---|
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Representative Procedure: The ingredients are mixed to form a suspension containing 10 mg of active ingredient per 10 mL of suspension.

FORMULATION EXAMPLE H

A dry powder for administration by inhalation is prepared as follows:

| Ingredients | Amount |
|---|---|
| Compound of the invention | 1.0 mg |
| Lactose | 25 mg |

Representative Procedure: The active ingredient is micronized and then blended with lactose. This blended mixture is then loaded into a gelatin inhalation cartridge. The contents of the cartridge are administered using a powder inhaler.

FORMULATION EXAMPLE I

A dry powder for administration by inhalation in a metered dose inhaler is prepared as follows:

Representative Procedure: A suspension containing 5 wt. % of a compound of the invention and 0.1 wt. % lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into cartridges with pressurized 1,1,1,2-tetrafluoroethane.

FORMULATION EXAMPLE J

An injectable formulation is prepared as follows:

| Ingredients | Amount |
|---|---|
| Compound of the invention | 0.2 g |
| Sodium acetate buffer solution (0.4 M) | 40 mL |
| HCl (0.5 N) or NaOH (0.5 N) | q.s. to pH 4 |
| Water (distilled, sterile) | q.s. to 20 mL |

Representative Procedure: The above ingredients are blended and the pH is adjusted to 4±0.5 using 0.5 N HCl or 0.5 N NaOH.

FORMULATION EXAMPLE K

Capsules for oral administration are prepared as follows:

| Ingredients | Amount |
|---|---|
| Compound of the Invention | 4.05 mg |
| Microcrystalline cellulose (Avicel PH 103) | 259.2 mg |
| Magnesium stearate | 0.75 mg |

Representative Procedure: The ingredients are thoroughly blended and then loaded into a gelatin capsule (Size #1, White, Opaque) (264 mg of composition per capsule).

FORMULATION EXAMPLE L

Capsules for oral administration are prepared as follows:

| Ingredients | Amount |
|---|---|
| Compound of the Invention | 8.2 mg |
| Microcrystalline cellulose (Avicel PH 103) | 139.05 mg |
| Magnesium stearate | 0.75 mg |

Representative Procedure: The ingredients are thoroughly blended and then loaded into a gelatin capsule (Size #1, White, Opaque) (148 mg of composition per capsule).

It will be understood that even those pharmaceutical compositions in which the crystallinity of the compound is not maintained, for example, solution formulations, are advantageously prepared from compound 1 in a crystalline form.

Utility

The benzimidazole-carboxamide compound of the invention is a 5-$HT_4$ receptor agonist and therefore is expected to be useful for treating medical conditions mediated by 5-$HT_4$ receptors or associated with 5-$HT_4$ receptor activity, i.e. medical conditions which are ameliorated by treatment with a 5-$HT_4$ receptor agonist. Such medical conditions include, but are not limited to, irritable bowel syndrome (IBS), chronic constipation, functional dyspepsia, delayed gastric emptying, gastroesophageal reflux disease (GERD), gastroparesis, post-operative ileus, intestinal pseudo-obstruction, and drug-induced delayed transit. In addition, it has been suggested that some 5-$HT_4$ receptor agonist compounds may be used in the treatment of central nervous system disorders including cognitive disorders, behavioral disorders, mood disorders, and disorders of control of autonomic function.

In particular, the compound of the invention increases motility of the gastrointestinal (GI) tract and thus is expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and the compound of the invention.

When used to treat disorders of reduced motility of the GI tract or other conditions mediated by 5-$HT_4$ receptors, the compound of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by 5-$HT_4$ receptors will range from about 0.0007 to about 20 mg/kg/day of active agent, including from about 0.0007 to about 1 mg/kg/day. For an average 70 kg human, this would amount to from about 0.05 to about 70 mg per day of active agent.

In one aspect of the invention, the compound of the invention is used to treat chronic constipation. When used to treat chronic constipation, the compound of the invention will typically be administered orally in a single daily dose or in multiple doses per day. Preferably, the dose for treating chronic constipation will range from about 0.05 to about 70 mg per day.

In another aspect of the invention, the compound of the invention is used to treat irritable bowel syndrome. When used to treat constipation-predominant irritable bowel syndrome, the compound of the invention will typically be administered orally in a single daily dose or in multiple doses per day. Preferably, the dose for treating constipation-predominant irritable bowel syndrome will range from about 0.05 to about 70 mg per day.

In another aspect of the invention, the compound of the invention is used to treat diabetic gastroparesis. When used to treat diabetic gastroparesis, the compound of the invention will typically be administered orally in a single daily dose or in multiple doses per day. Preferably, the dose for treating diabetic gastroparesis will range from about 0.05 to about 70 mg per day.

In yet another aspect of the invention, the compound of the invention is used to treat functional dyspepsia. When used to treat functional dyspepsia, the compound of the invention will typically be administered orally in a single daily dose or in multiple doses per day. Preferably, the dose for treating functional dyspepsia will range from about 0.05 to about 70 mg per day.

The invention also provides a method of treating a mammal having a disease or condition associated with 5-$HT_4$ receptor activity, the method comprising administering to the mammal a therapeutically effective amount of the compound of the invention or of a pharmaceutical composition comprising a compound of the invention.

As described above, the compound of the invention is a 5-$HT_4$ receptor agonist. The invention further provides, therefore, a method of agonizing a 5-$HT_4$ receptor in a mammal, the method comprising administering the compound of the invention to the mammal.

Among other properties, the compound of the invention has been found to be a potent agonist of the 5-$HT_4$ receptor and to exhibit exceptional selectivity for the 5-$HT_4$ receptor subtype over the 5-$HT_3$ receptor subtype in radioligand binding assays. Further, the compound of the invention has demonstrated superior pharmacokinetic properties in a rat model. The compound is thus expected to be highly bioavailable upon oral administration. In addition, the compound has been shown not to exhibit an unacceptable level of inhibition of the potassium ion current in an in vitro voltage-clamp model using isolated whole cells expressing the hERG cardiac potassium channel. The voltage-clamp assay is an accepted pre-clinical method of assessing the potential for pharmaceutical agents to change the pattern of cardiac repolarization, specifically to cause, so-called QT prolongation, which has been associated with cardiac arrhythmia. (Cavero et al., *Opinion on Pharmacotherapy*, 2000, 1, 947-73, Fermini et al., *Nature Reviews Drug Discovery*, 2003, 2, 439-447) Accordingly, pharmaceutical compositions comprising the compound of the invention are expected to have an acceptable cardiac profile.

There properties, as well as the utility of the compound of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl

DMSO=dimethyl sulfoxide

MeCN=acetonitrile

TFA=trifluoroacetic acid $R_f$=retention factor

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

Preparation 1: Synthesis of
2-isopropyl-1H-benzoimidazole-4-carboxylic acid (piperidin-4-ylmethyl)amide a. Preparation of 2,3-diaminobenzoic acid methyl ester To a nitrogen-saturated solution of 2-amino-3-nitrobenzoic acid methyl ester (Chess GmbH, 50 g, 0.26 mol) in absolute ethanol (800 mL) was added palladium hydroxide (Degussa, 20% w/w on carbon, 58.75% w/w water, 10 g). The slurry was degassed then shaken vigorously under hydrogen (4 atm) at room temperature for 48 h. The catalyst was filtered and the filtrate concentrated in vacuo to afford 2,3-diaminobenzoic acid methyl ester as a dark orange oil that solidified on standing (43 g, 0.26 mol, 100%). (m/z): [M-OCH$_3$]$^+$ calcd for C$_8$H$_{10}$N$_2$O$_2$ 135.05; found 135.3. $^1$H NMR (300 MHz, DMSO-d$_6$): δ (ppm) 3.74 (s, 3H), 4.80 (br s, 1H), 6.20 (br s, 1H), 6.38 (t, 1H), 6.70 (d, 1H), 7.06 (d, 1H).

b. Preparation of 2-isopropyl-1H-benzoimidazole-4-carboxylic acid

A slurry of 2,3-diaminobenzoic acid methyl ester (21.5 g, 0.13 mol) and isobutyric acid (36.2 mL, 0.39 mol) in aqueous hydrochloric acid (4M, 210 mL) was stirred under reflux for 24 h to afford a homogenous solution. The solution was cooled to 10° C. and the pH raised to 3.5 using aqueous sodium hydroxide solution (4M, approx. 210 mL), while maintaining the temperature below 30° C. The reaction mixture was stirred at room temperature for 2 h, cooled to 10° C., and the resultant precipitate filtered off. The solid cake was transferred to a beaker and acetonitrile (300 mL) was added. The slurry was stirred at room temperature for 1 h then and filtered to afford a grey solid. The solid was dried under vacuum to afford the title intermediate (23 g, 0.1 l mol, 87%). (m/z): [M+H]$^+$ calcd for C$_{11}$H$_{12}$N$_2$O$_2$ calcd. 205.09; found 205.3. $^1$H NMR (300 MHz, DMSO-d$_6$): δ (ppm) 1.27 (d, 6H), 3.39 (m, 1H), 7.29 (t, 1H), 7.78 (m, 2H).

c. Preparation of 4-{[(2-isopropyl-1H-benzoimidazole-4-carbonyl)amino]methyl}-piperidine-1-carboxylic acid tert-butyl ester To a solution of 2-isopropyl-1H-benzoimidazole-4-carboxylic acid (9.0 g, 44.1 mmol) in anhydrous N,N-dimethylformamide (100 mL) was added 4-aminomethyl-piperidine-1-carboxylic acid tert-butyl ester (9.4 g, 44.1 mmol), followed by N, N-diisopropylethylamine (16.9 mL, 97.0 mmol). The solution was stirred for 15 min at room temperature prior to the addition of hydroxybenzotriazole (5.9 g, 44.1 mmol), N-Ethyl-N'-(3-dimethylaminopropyl)carbodiimide hydrochloride (8.4 g, 44.1 mmol), and additional N,N-dimethylformamide (50 mL). The reaction mixture was stirred at room temperature for 16 h, diluted with dichloromethane (300 mL), and washed sequentially with 1M aqueous phosphoric acid, 1M aqueous sodium hydroxide and brine. The solution was then dried over sodium sulfate and concentrated in vacuo to afford brown oil which solidified upon addition of hexanes. The solid was filtered to give the title intermediate as a beige solid (13.8 g, 36.0 mmol, 78%). (m/z): [M+H]$^+$ calcd for C$_{22}$H$_{32}$N$_4$O$_3$ 401.26; found 401.5; [M-Boc+H]$^+$ 301.5. Retention time (anal. HPLC: 2-90% MeCN/H$_2$O over 6 min)=3.7 min. $^1$H NMR (300 MHz, DMSO-d$_6$): δ (ppm) 1.20 (m, 2H), 1.37 (s, 9H), 1.37 (s, 6H), 1.72 (m, 1H), 1.75 (m, 2H), 2.73 (br s, 2H), 3.22 (septet, 1H), 3.36 (m, 2H), 3.95 (m, 2H), 7.26 (t, 1H), 7.63 (d, 1H), 7.79 (d, 1H), 10.11 (t, 1H).

d. Synthesis of 2-isopropyl-1H-benzoimidazole-4-carboxylic acid (piperidin-4-ylmethyl)amide To a solution of 4-{[(2-isopropyl-1H-benzoimidazole-4-carbonyl)amino]methyl}-piperidine-1-carboxylic acid tert-butyl ester (10.8 g, 27.0 mmol) dissolved in dichloromethane (50 mL) at 0° C. was slowly added trifluoroacetic acid (50 mL) in 5 mL portions. The solution was allowed to warm to room temperature, stirred for an additional 20 minutes then evaporated in vacuo. Excess trifluoroacetic acid was removed by co-evaporation with toluene. The residue was then dissolved in a minimal volume of dichloromethane and slowly added to diethyl ether (1 L) at 0° C. The resulting slurry was stirred for 2 h at room temperature then filtered to afford the bis-trifluoroacetate salt of the title compound as a light brown solid (12.7 g, 24.0 mmol, 89%). (m/z): [M+H]$^+$ calcd for C$_{17}$H$_{24}$N$_4$O 301.21; found 301.5. Retention time (anal. HPLC: 2-50% MeCN/H$_2$O over 6 min)=1.65 min. $^1$H NMR (300 MHz, MeOD-d$_3$): δ (ppm) 1.59 (d, 6H), 1.60 (m, 1H), 2.03 (m, 2H), 2.04 (m, 1H), 3.00 (m, 2H), 3.43 (m, 2H), 3.45 (m, 2H), 3.63 (septet, 1H), 7.63 (t, 1H), 7.90 (d, 1H), 7.96 (d, 1H), 9.04 (t, 1H).

Preparation 2: Synthesis of
4-formylpiperidine-1-carboxylic acid methyl ester a. Preparation of 4-hydroxymethyl-piperidine-1-carboxylic acid methyl ester 4-Hydroxymethylpiperidine (1.0 g, 8.6 mmol) was dissolved in water (15 mL) and cooled to 0° C. To this solution was added dropwise a solution of potassium carbonate (4.8 g, 34.7 mmol) in water (10 mL), followed by methyl chloroformate (2.68 mL, 34.7 mmol). The mixture was stirred vigorously and allowed to warm to room temperature over 2 h. After stirring overnight (16 h), the reaction mixture was acidified with 6M aqueous hydrochloric acid and extracted with dichloromethane (3×60 mL). The extracts were combined, dried over sodium sulfate and filtered. The filtrate was evaporated to yield the title intermediate (1.4 g, 8.1 mmol, 93%) as a colorless oil. (m/z): C$_8$H$_{15}$NO$_3$ calcd. 173.11; found 156.2 [M-H$_2$O+H]$^+$. $^1$H NMR (300 MHz, DMSO-d$_6$): δ (ppm) 0.98 (m, 2H), 1.52 (m, 1H), 1.63 (br d, 2H), 2.72 (br m, 2H), 3.23 (d, 2H), 3.56 (s, 3H), 3.95 (br d, 2H), 4.48 (br s, 1H).

b. Synthesis of 4-formylpiperidine-1-carboxylic acid methyl ester

To a solution of oxalyl chloride (4.1 mL, 8.2 mmol) in dichloromethane (4 mL) at −78° C. was added dropwise a solution of dimethylsulfoxide (1.2 mL, 16.4 mmol) in dichloromethane (4 mL). After stirring for 5 min, a solution of 4-hydroxymethyl-piperidine-1-carboxylic acid methyl ester (1.3 g, 7.5 mmol) in dichloromethane (5 mL) was added. The resulting solution was stirred for another 5 min, then triethylamine (5.2 mL, 37.3 mmol) was added and the mixture allowed to warm to −10° C. After stirring for 1 h, dichloromethane (100 mL) was added, and the organic layer was washed with 1M aqueous phosphoric acid, 1M aqueous sodium hydroxide, and brine. The solution was dried over sodium sulfate then evaporated to afford the title intermediate as a wheat colored oil (1.0 g, 5.8 mmol, 78%). $^1$H NMR (300 MHz, DMSO-d$_6$): δ (ppm) 1.36 (m, 2H), 1.83 (m, 2H), 2.48 (br m, 1H), 2.93 (br t, 2H), 3.56 (s, 3H), 3.80 (br d, 2H), 9.56 (s, 1H).

Example 1

Synthesis of 4-(4-{[(2-isopropyl-1H-benzoimidazole-4-carbonyl)-amino]methyl}piperidin-1-ylmethyl)piperidine-1-carboxylic acid methyl ester 2-Isopropyl-1H-benzoimidazole-4-carboxylic acid (piperidin-4-ylmethyl)amide, (bis TFA salt; 1.1 g, 2.0 mmol) was suspended in dichloromethane (20 mL) and N,N-diisopropylethylamine (0.72 mL, 4.0 mmol) was added. When the suspension became a clear solution, acetic acid (0.13 mL, 2.0 mmol) was added, followed by a solution of 4-formylpiperidine-1-carboxylic acid methyl ester (0.54 g, 3.1 mmol) in dichloromethane (20 mL). After stirring for 5 minutes at room temperature, sodium triacetoxyborohydride (0.628 g, 3.1 mmol) was added, and the reaction stirred for an additional 1 h. The aqueous layer was then made alkaline with 1M aqueous sodium hydroxide (35 mL) and extracted with dichloromethane (2×20 mL). The combined organic layers were washed with brine, dried over sodium sulfate and evaporated to yield crude product as a brown solid (1.41 g).

The crude product was purified via preparative HPLC (reverse phase) [gradient of 5-10-25%:5% MeCN/water (0.1% TFA) to 10% MeCN linear over 10 min; 10% MeCN to 25% MeCN linear over 50 min; flow rate=15 mumin; detection at 280 nm] to provide the title compound as the bis trifluoroacetate salt, which was then lyophilized. A mixture of 1 M sodium hydroxide and dichloromethane (1:1, 100 mL) was added to the lyophilized bis trifluoroacetate salt. The organic layer was dried over sodium sulfate, filtered, and evaporated, and the resulting solid was lyophilized to provide the title compound as a white solid (0.93 g, 2 mmol, 98% yield, purity 97.5%). (m/z): [M+H]+ calcd for $C_{25}H_{37}N_5O_3$ 456.30; found 456.3. Retention time (anal. HPLC: 2-50% MeCN/H$_2$O over 6 min)=3.06 min. $^1$H NMR (300 MHz, DMSO- d$_6$): 0.92 (m, 2H), 1.30 (m, 2H), 1.38 (d, 6H), 1.53 (m, 1H), 1.60-1.90 (m, 7H), 2.07 (d, 2H), 2.73 (br m, 2H), 2.83 (br d, 2H), 3.22 (septet, 1H), 3.33 (t, 2H), 3.56 (s, 3H), 3.93 (br d, 2H), 7.23 (t, 1H), 7.62(d, 1H), 7.77 (d, 1H), 10.10 (br s, 1H).

Example 2

Synthesis of crystalline 4-(4-{[(2-isopropyl-1H-benzoimidazole-4-carbonyl)-amino]methyl}piperidin-1-ylmethyl)piperidine-1-carboxylic acid methyl ester (Form I)

4-(4-{[(2-isopropyl-1H-benzoimidazole-4-carbonyl)-amino]methyl}piperidin-1-ylmethyl)piperidine-1-carboxylic acid methyl ester in amorphous solid form, prepared according to the process of Example 1 (300 mg) was dissolved in acetonitrile (15 mL), mixed until complete dissolution, and exposed to the atmosphere resulting in partial evaporation. Crystals were observed to have nucleated within 2 h. Chemical composition of the crystals was confirmed by $^1$H NMR, liquid chromatography/mass spectrometry (LC/MS), and x-ray structure analysis. Crystalline nature of the solid product was confirmed by powder x-ray diffraction, differential scanning calorimetry, and x-ray diffraction analysis of crystal structure.

Example 3

Synthesis of crystalline 4-(4-{[(2-isopropyl-1H-benzoimidazole-4-carbonyl)-amino]methyl}piperidin-1-ylmethyl)piperidine-1-carboxylic acid methyl ester (Form I)

a. Preparation of 4-hydroxymethyl-piperidine-1-carboxylic acid methyl ester

4-Hydroxymethylpiperidine (47.6 g, 1.0 eq) and water (300 mL) were charged to a flask. The resulting mixture was cooled to 0-10° C. Potassium carbonate (85.7 g, 1.5 eq) dissolved in water (150 mL) and methyl chloroformate (38.4 mL, 1.1 eq) were added while maintaining the temperature at below 10° C. When the addition was complete, the reaction mixture was warmed up to 20-30° C. for 1 hour. After the reaction was complete, dichloromethane (500 mL) was added to the reaction mixture. The organic layer was collected and washed with 1 M phosphoric acid solution (200 mL), saturated sodium bicarbonate solution (200 mL) and saturated sodium chloride solution (200 mL). The organic layer was dried over sodium sulfate (50 g, 1 w/w eq) and then distilled under vacuum to produce the title intermediate. (67.0 g, 90% yield)

b. Preparation of 4-formylpiperidine-1-carboxylic acid methyl ester

4-Hydroxymethylpiperidine-1-carboxylic acid methyl ester (34.7 g, 1.0 eq) was dissolved in dichloromethane and cooled to 0-10° C. A solution of sodium bicarbonate (2.35 g, 0.14 eq) and sodium bromide (2.40 g, 0.10 eq) in water (100 mL) was added over 15 min while maintaining the temperature at 0-10° C. 2,2,6,6-Tetramethyl-1-piperidinyloxy free radical (TEMPO) (0.32 g, 0.01 eq) was added to the mixture, followed by 10-13% w/v sodium hypochlorite solution (135 mL, 1.1 eq) over 1 h with good agitation while maintaining the temperature at 0-10° C. After the reaction was complete, the layers were separated and the organic layer washed with water (150 mL) and dried over sodium sulfate (30 g, 1 w/w eq). The solvent was removed by distillation to provide the title intermediate. (31.0 g, 90% yield)

c. Preparation of 2-isopropyl-1H-benzoimidazole-4-carboxylic acid (piperidin-4-ylmethyl)amide Trifluoroacetic acid (56.0 mL, 10 eq) was added to a flask containing a ~5° C. solution of 4-{[(2-isopropyl-1H-benzoimidazole-4-carbonyl)amino]methyl}-piperidine-1-carboxylic acid tert-butyl ester (30.0 g, 1.0 eq) in dichloromethane (300 mL) while maintaining the temperature below 10° C. The resulting mixture was stirred at 20-30° C. for 2 h. When the reaction was complete, triethylamine (73.2 mL, 7.0 eq) and acetic acid (4.3 mL, 1.0 eq) were added to provide a solution of the title intermediate with an apparent pH of approximately 4 that was used directly in the next step.

d. Synthesis of 4-(4-{[(2-isopropyl-1H-benzoimidazole-4-carbonyl)-amino]methyl}piperidin-1-ylmethyl)piperidine-1-carboxylic acid methyl ester 4-Formylpiperidine-1-carboxylic acid methyl ester (25.7 g, 2.0 eq) was added to the solution prepared in the previous step while maintaining the temperature at 20-30° C. After stirring for 30 min, sodium triacetoxyborohydride (24.3 g, 1.5 eq) was added while maintaining the temperature at 20-30° C. The reaction mixture was stirred at 20-30° C. for 30 min. After the reaction was complete, 1 M hydrochloric acid (300 mL) was added to quench the reaction. The product-containing aqueous layer was collected and washed with dichloromethane (150 mL). The aqueous layer was treated with activated carbon (Darco G60, 6 g, 20% w/w) to remove color.

The suspension was stirred for 1 hr, and then filtered through a bed of Celite. Dichloromethane (300 mL) was added to the aqueous solution and the product free-based using 4 N sodium hydroxide by adjusting the pH of the aqueous layer to 12-13. The organic layer was collected and washed with water (300 mL). The organic layer was distilled at 80° C. and solvent exchanged with acetonitrile (2×300 mL), to remove dichloromethane and residual triethylamine. The solids were suspended in acetonitrile (600 mL), and the mixture heated until the solids were dissoved (~75° C.). The solution was cooled until nucleation occured (~55-65° C.) and held for 1 h. The slurry was cooled to 20° C. over 2 h, and then to 0-5° C. over 30 min, followed by stirring at 0-5° C. for 30 min. The solids were filtered and washed with cold acetonitrile (60 mL). The wet cake was dried under vacuum at 60° C. for 6 h to provide the title compound. (28.3 g, 85% yield).

Example 4

Synthesis of crystalline 4-(4-{[(2-isopropyl-1H-benzoimidazole-4-carbonyl)-amino]methyl}piperidin-1-ylmethyl)piperidine-1-carboxylic acid methyl ester (Form I)

4-(4-{[(2-isopropyl-1H-benzoimidazole-4-carbonyl)-amino]methyl}piperidin-1-ylmethyl)piperidine-1-carboxylic acid methyl ester in amorphous solid form, prepared according to the process of Example 1 was dispersed in the inert diluents listed in Table I below. The mixtures were exposed to the atmosphere and allowed to completely evaporate. The resulting solids were characterized by powder x-ray diffraction. All solids were demonstrated to be crystalline with a powder x-ray diffraction pattern consistent with that reported below in Example 7, which was obtained from the sample of Example 2.

TABLE I

Crystalline Form Synthesis

| Diluent | Compound of Formula (I) (mg) | Volume of Diluent (mL) |
|---|---|---|
| Ether | 4.60 | 0.230 |
| Cyclohexane | 4.87 | 0.486 |
| Ethyl acetate | 5.67 | 0.284 |

Example 5

Synthesis of crystalline 4-(4-{[(2-isopropyl-1H-benzoimidazole-4-carbonyl)-amino]methyl}piperidin-1-ylmethyl)piperidine-1-carboxylic acid methyl ester (Form II)

4-(4-{[(2-Isopropyl-1H-benzoimidazole-4-carbonyl)-amino]methyl}piperidin-1-ylmethyl)piperidine-1-carboxylic acid methyl ester in amorphous solid form (42.2 mg), was dispersed in hexane (4.22 mL) at ambient temperature to a final concentration of 10 mg/mL. The solution was sonicated to disperse larger solids. After 24 h at ambient temperature (approximately 22° C.) crystallization had occurred. The crystalline solids were isolated via vacuum filtration, prior to analysis.

Example 6

Synthesis of crystalline 4-(4-{[(2-isopropyl-1H-benzoimidazole-4-carbonyl)-amino]methyl}piperidin-1-ylmethyl)piperidine-1-carboxylic acid methyl ester (Form III)

4-(4-{[(2-Isopropyl-1H-benzoimidazole-4-carbonyl)-amino]methyl}piperidin-1-ylmethyl)piperidine-1-carboxylic acid methyl ester in amorphous solid form (38 mg) was dissolved in a 1:1 ethanol:water solvent mixture (1.9 mL) at ambient temperature to a final concentration of 20 mg/mL. The solution was sonicated for 30 seconds to ensure complete dissolution. The solution was then left to slowly evaporate in an uncapped vial. After 24 h at ambient temperature crystallization had occurred. The crystalline solids were isolated via vacuum filtration. The filter cake was washed once with a 1:1 ethanol:water solvent mixture, prior to analysis.

Example 7

Powder X-Ray Diffraction

Powder x-ray diffraction patterns were obtained with a Thermo ARL X-Ray Diffractometer Model X'TRA (Thermo ARL SA, Switzerland) using Cu Kα radiation at 1.542 Å (45 kV, 40 mA) with a Si(Li) solid-state detector. The analysis was typically performed at a scan rate of 2°/min with a step size of 0.03° per point over a range of 2° to 35° in two-theta angle. Samples, either as received or ground to a fine powder, were gently packed into a quartz insert 7.8 mm in diameter and 0.5 mm in depth designed to fit into the instrument top-loading sample cup for analysis. The instrument calibration to within ±0.02° two-theta angle was verified weekly by comparison with a silicon metal standard. A representative PXRD pattern for the crystalline compound of Example 2 (Form I), which was hand ground to a powder, is shown in FIG. 1. A representative PXRD pattern for a sample of crystalline Form III obtained with a Rigaku diffractometer using Cu Kα (30 kV, 15 mA) radiation is shown in FIG. 5.

Example 8

X-Ray Structure Analysis a. Form I

A chunk crystal produced in Example 2 having dimensions of 0.33×0.17×0.11 mm was mounted on a glass fiber. X-ray structure data was obtained using a Bruker SMART 6K CCD-ray area detector with window diameter of 13.5 cm, controlled by SMART version 5.630 software (Bruker, 2003) using Cu Kα radiation. The sample to detector distance was 5.039 cm. Data was collected at a temperature of −153±1° C. and was analyzed using SHELXS version 6.14 (Bruker, 2003) software. The following lattice parameters were derived: unit cell is orthorhombic with dimensions a=16.9053 Å, b=9.5172 Å, c=15.4659 Å; space group is $Pna2_1$; calculated density is 1.22 g/cm. Powder x-ray diffraction peaks predicted from the derived atomic positions are in excellent agreement with the observed results obtained as described in Example 7, as shown in Table II.

TABLE II

PXRD Peak Positions

| Observed 2θ (degrees) | Predicted 2θ (degrees) |
|---|---|
| 15.08 ± 0.20 | 15.1 ± 0.2 |
| 15.41 ± 0.20 | 15.6 ± 0.2 |
| 19.00 ± 0.20 | 19.2 ± 0.2 |
| 19.70 ± 0.20 | 19.5 ± 0.2 |
| 23.68 ± 0.20 | 23.7 ± 0.2 | b. Form III

A chunk crystal produced by the process of Example 6 having dimensions of 0.35×0.12×0.09 mm was analyzed by the method described above. The following lattice parameters were derived: unit cell is monoclinic with dimensions a=14.8101 Å, b=9.9985 Å, c=17.9222 Å; β=106.3020°, space group is $P2_1/n$; calculated density is 1.23 g/cm³.

Example 9

Thermal Analysis

Differential scanning calorimetry (DSC) was performed using a TA Instruments Model Q-100 module. Data were collected and analyzed using TA Instruments Thermal Advantage for Q Series™ software. A sample of about 7 mg was accurately weighed into an aluminum pan with lid. The sample was evaluated using a linear heating ramp of 10° C./min from 5° C. to about 200° C. The DSC cell was purged with dry nitrogen during use.

Thermogravimetric analysis (TGA) was performed using a TA Instruments Model Q-500 module. Data were collected and analyzed using TA Instruments Thermal Advantage for Q Series™ software. A sample weighing about 2 mg was placed in an aluminum pan on a platinum cradle and scanned from ambient temperature to about 300° C. with a linear heating rate of 10° C./min. The balance and furnace chambers were purged with nitrogen during use.

Representative DSC and TGA traces for crystalline Form I (prepared according to the process of Example 3), Form II, and Form III material are shown in FIGS. 2, 4, and 6, respectively.

Example 10

Dynamic Moisture Sorption Assessment

Dynamic moisture sorption (DMS) assessment was performed at 25° C. using a VTI atmospheric microbalance, SGA-100 system (VTI Corp., Hialeah, Fla. 33016). A sample size of approximately 5-10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (+5% RH) when the mass of the sample was stable to within 0.02% for 5 consecutive points. A representative DMS isotherm for the crystalline compound of Example 2 (Form I) is shown in FIG. 3.

The crystalline compound of the invention exhibits a reversible sorption/desorption profile with a weight change of less than 0.25% over the entire range of 2% to 90% RH and a weight change of less than 0.1% over the critical humidity range of 40% to 75% RH.

Example 11

Infrared Analysis

The infrared (IR) absorption spectrum of the crystalline compound of Example 2 (Form I) was determined over the frequency range 4000 to 675 cm⁻¹ using an Avatar 360 FT-IR spectrometer equipped with a Nicolet attenuated total reflection (ATR) sample holder. A representative IR absorption spectrum for a sample of the crystalline compound of the invention had significant absorption bands at 766±1, 1097±1, 1251±1, 1413±1, 1449±1, 1579±1, 1609±1, 1640±1, and 1696±1 cm⁻¹.

Example 12

Solid State Stability Assessment

Samples of the crystalline compound of Form I, prepared according to the process of Example 3, were stored in multiple open glass vials at 40° C. and 75% RH. At specific intervals, the contents of a representative vial was removed and analyzed by DSC, TGA, PXRD, and by HPLC for chemical purity. After three months of storage, there was no detectable change in the DSC or TGA thermograms nor in the PXRD pattern. The chemical purity of the stored sample was 99.5%.

Assay 1: Radioligand Binding Assay on 5-HT$_{4(c)}$ Human Receptors a. Membrane Preparation 5-HT$_{4(c)}$ HEK-293 (human embryonic kidney) cells stably-transfected with human 5-HT$_{4(c)}$ receptor cDNA (Bmax=~6.0 pmol/mg protein, as determined using [³H]-GR113808 membrane radioligand binding assay) were grown in T-225 flasks in Dulbecco's Modified Eagles Medium (DMEM) containing 4,500 mg/L D-glucose and pyridoxine hydrochloride (GIBCO-Invitrogen Corp., Carlsbad Calif.: Cat #11965) supplemented with 10% fetal bovine serum (FBS) (GIBCO-Invitrogen Corp.: Cat #10437), 2 mM L-glutamine and (100 units) penicillin-(100 μg) streptomycin/ml (GIBCO-Invitrogen Corp.: Cat #15140) in a 5% CO$_2$, humidified incubator at 37° C. Cells were grown under continuous selection pressure by the addition of 800 μg/mL geneticin (GIBCO-Invitrogen Corp.: Cat # 10131) to the medium.

Cells were grown to roughly 60-80% confluency (<35 subculture passages). At 20-22 hours prior to harvesting, cells were washed twice and fed with serum-free DMEM. All steps of the membrane preparation were performed on ice. The cell monolayer was lifted by gentle mechanical agitation and trituration with a 25 mL pipette. Cells were collected by centrifugation at 1000 rpm (5 min).

For the membrane preparation, cell pellets were resuspended in ice-cold 50 mM 4-(2-hydroxyethyl)-1-piperazineethanesulphonic acid (HEPES), pH 7.4 (membrane preparation buffer) (40 mL/total cell yield from 30-40 T225 flasks) and homogenized using a polytron disrupter (setting 19, 2×10 s) on ice. The resultant homogenates were centrifuged at 1200 g for 5 min at 4° C. The pellet was discarded and the supernatant centrifuged at 40,000 g (20 min). The pellet was washed once by resuspension with membrane preparation buffer and centrifugation at 40,000 g (20 min). The final pellet was resuspended in 50 mM HEPES, pH 7.4 (assay buffer) (equivalent 1 T225 flask/1 mL). Protein concentration of the membrane suspension was determined by the method of Bradford (Bradford, 1976). Membranes were stored frozen in aliquots at −80° C.

b. Radioligand Binding Assays

Radioligand binding assays were performed in 1.1 mL 96-deep well polypropylene assay plates (Axygen) in a total assay volume of 400 μL containing 2 μg membrane protein in 50 mM HEPES pH 7.4, containing 0.025% bovine serum albumin (BSA). Saturation binding studies for determination of $K_d$ values of the radioligand were performed using [$^3$H]-GR113808 (Amersham Inc., Bucks, UK: Cat #TRK944; specific activity ~82 Ci/mmol) at 8-12 different concentrations ranging from 0.001 nM-5.0 nM. Displacement assays for determination of $pK_i$ values of compounds were performed with [$^3$H]-GR113808 at 0.15 nM and eleven different concentrations of compound ranging from 10 pM-100 μM.

Test compounds were received as 10 mM stock solutions in DMSO and diluted to 400 μM into 50 mM HEPES pH 7.4 at 25° C., containing 0.1% BSA, and serial dilutions (1:5) then made in the same buffer. Non-specific binding was determined in the presence of 1 μM unlabeled GR113808. Assays were incubated for 60 min at room temperature, and then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH 7.4) to remove unbound radioactivity. Plates were dried, 35 μL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed by nonlinear regression analysis with the GraphPad Prism Software package (GraphPad Software, Inc., San Diego, Calif.) using the 3-parameter model for one-site competition. The BOTTOM (curve minimum) was fixed to the value for nonspecific binding, as determined in the presence of 1 μM GR113808. $K_i$ values for test compounds were calculated, in Prism, from the best-fit $IC_{50}$ values, and the $K_d$ value of the radioligand, using the Cheng-Prusoff equation (Cheng and Prusoff, *Biochemical Pharmacology*, 1973, 22, 3099-108): $K_i=IC_{50}/(1+[L]/K_d)$ where [L]=concentration [$^3$H]-GR113808. Results are expressed as the negative decadic logarithm of the $K_i$ values, $pK_i$.

Test compounds having a higher $pK_i$ value in this assay have a higher binding affinity for the 5-HT$_4$ receptor. The compound of the invention had a $pK_i$ value above about 9.

Assay 2: Radioligand Binding Assay on 5-HT$_{3A}$ Human Receptors: Determination of Receptor Subtype Selectivity a. Membrane Preparation 5-HT$_{3A}$ HEK-293 (human embryonic kidney) cells stably-transfected with human 5-HT$_{3A}$ receptor cDNA were obtained from Dr. Michael Bruess (University of Bonn, GDR) (Bmax=~9.0 pmol/mg protein, as determined using [$^3$H]-GR65630 membrane radioligand binding assay). Cells were grown in T-225 flasks or cell factories in 50% Dulbecco's Modified Eagles Medium (DMEM) (GIBCO-Invitrogen Corp., Carlsbad, Calif.: Cat #111965) and 50% Ham's F12 (GIBCO-Invitrogen Corp.: Cat #11765) supplemented with 10% heat inactivated fetal bovine serum (FBS) (Hyclone, Logan, Utah: Cat #SH30070.03) and (50 units) penicillin-(50 μg) streptomycin/ml (GIBCO-Invitrogen Corp.: Cat #15140) in a 5% $CO_2$, humidified incubator at 37° C.

Cells were grown to roughly 70-80% confluency (<35 subculture passages). All steps of the membrane preparation were performed on ice. To harvest the cells, the media was aspirated and cells were rinsed with $Ca^{2+}$, $Mg^{2+}$-free Dulbecco's phosphate buffered saline (dPBS). The cell monolayer was lifted by gentle mechanical agitation. Cells were collected by centrifugation at 1000 rpm (5 min). Subsequent steps of the membrane preparation followed the protocol described above for the membranes expressing 5-HT$_{4(c)}$ receptors.

b. Radioligand Binding Assays

Radioligand binding assays were performed in 96-well polypropylene assay plates in a total assay volume of 200 μL containing 1.5-2 μg membrane protein in 50 mM HEPES pH 7.4, containing 0.025% BSA assay buffer. Saturation binding studies for determination of $K_d$ values of the radioligand were performed using [$^3$H]-GR65630 (PerkinElmer Life Sciences Inc., Boston, Mass.: Cat #NET1011, specific activity ~85 Ci/mmol) at twelve different concentrations ranging from 0.005 nM to 20 nM. Displacement assays for determination of $pK_i$ values of compounds were performed with [$^3$H]-GR65630 at 0.50 nM and eleven different concentrations of compound ranging from 10 pM to 100 μM. Compounds were received as 10 mM stock solutions in DMSO (see section 3.1), diluted to 400 μM into 50 mM HEPES pH 7.4 at 25° C., containing 0.1% BSA, and serial (1:5) dilutions then made in the same buffer. Non-specific binding was determined in the presence of 10 μM unlabeled MDL72222. Assays were incubated for 60 min at room temperature, then the binding reactions were terminated by rapid filtration over 96-well GF/B glass fiber filter plates (Packard BioScience Co., Meriden, Conn.) presoaked in 0.3% polyethyleneimine. Filter plates were washed three times with filtration buffer (ice-cold 50 mM HEPES, pH 7.4) to remove unbound radioactivity. Plates were dried, 35 μL Microscint-20 liquid scintillation fluid (Packard BioScience Co., Meriden, Conn.) was added to each well and plates were counted in a Packard Topcount liquid scintillation counter (Packard BioScience Co., Meriden, Conn.).

Binding data were analyzed using the non-linear regression procedure described above to determine $K_i$ values. The BOTTOM (curve minimum) was fixed to the value for non-specific binding, as determined in the presence of 10 μM MDL72222. The quantity [L] in the Cheng-Prusoff equation was defined as the concentration [$^3$H]-GR65630.

Selectivity for the 5-HT$_4$ receptor subtype with respect to the 5-HT$_3$ receptor subtype was calculated as the ratio $K_i$(5-HT$_{3A}$)/$K_i$(5-HT$_{4(c)}$). The compound of the invention had a 5-HT$_4$/5-HT$_3$ receptor subtype selectivity above about 200,000.

Assay 3: Whole-Cell cAMP Accumulation Flashplate Assay with HEK-293 Cells Expressing Human 5-HT$_{4(c)}$ Receptors In this assay, the functional potency of a test compound was determined by measuring the amount of cyclic AMP produced when HEK-293 cells expressing 5-HT$_4$ receptors were contacted with different concentrations of test compound.

a. Cell Culture

HEK-293 (human embryonic kidney) cells stably-transfected with cloned human 5-HT$_{4(c)}$ receptor cDNA were prepared expressing the receptor at two different densities: (1) at a density of about 0.5-0.6 pmol/mg protein, as determined using a [$^3$H]-GR113808 membrane radioligand binding assay, and (2) at a density of about 6.0 pmol/mg protein. The cells were grown in T-225 flasks in Dulbecco's Modified Eagles Medium (DMEM) containing 4,500 mg/L D-glucose (GIBCO-Invitrogen Corp.: Cat #11965) supplemented with 10% fetal bovine serum (FBS) (GIBCO-Invitrogen Corp.: Cat #10437) and (100 units) penicillin-(100 μg) streptomycin/ml (GIBCO-Invitrogen Corp.: Cat #15140) in a 5% $CO_2$, humidified incubator at 37° C. Cells were grown under continuous selection pressure by the addition of geneticin (800 µg/mL: GIBCO-Invitrogen Corp.: Cat #10131) to the medium.

b. Cell Preparation

Cells were grown to roughly 60-80% confluency. Twenty to twenty-two hours prior to assay, cells were washed twice, and fed, with serum-free DMEM containing 4,500 mg/L D-glucose (GIBCO-Invitrogen Corp.: Cat #11965). To harvest the cells, the media was aspirated and 10 mL Versene (GIBCO-Invitrogen Corp.: Cat #15040) was added to each T-225 flask. Cells were incubated for 5 min at RT and then dislodged from the flask by mechanical agitation. The cell suspension was transferred to a centrifuge tube containing an equal volume of pre-warmed (37° C.) dPBS and centrifuged for 5 min at 1000 rpm. The supernatant was discarded and the pellet was re-suspended in pre-warmed (37° C.) stimulation buffer (10 mL equivalent per 2-3 T-225 flasks). This time was noted and marked as time zero. The cells were counted with a Coulter counter (count above 8 µm, flask yield was $1-2 \times 10^7$ cells/flask). Cells were resuspended at a concentration of $5 \times 10^5$ cells/ml in pre-warmed (37° C.) stimulation buffer (as provided in the flashplate kit) and preincubated at 37° C. for 10 min.

cAMP assays were performed in a radioimmunoassay format using the Flashplate Adenylyl Cyclase Activation Assay System with $^{125}$I-cAMP (SMP004B, PerkinElmer Life Sciences Inc., Boston, Mass.), according to the manufacturer's instructions.

Cells were grown and prepared as described above. Final cell concentrations in the assay were $25 \times 10^3$ cells/well and the final assay volume was 100 µL. Test compounds were received as 10 mM stock solutions in DMSO, diluted to 400 µM into 50 mM HEPES pH 7.4 at 25° C., containing 0.1% BSA, and serial (1:5) dilutions then made in the same buffer. Cyclic AMP accumulation assays were performed with 11 different concentrations of compound ranging from 10 pM to 100 µM (final assay concentrations). A 5-HT concentration-response curve (10 pM to 100 µM) was included on every plate. The cells were incubated, with shaking, at 37° C. for 15 min and the reaction terminated by addition of 100 µl of ice-cold detection buffer (as provided in the flashplate kit) to each well. The plates were sealed and incubated at 4° C. overnight. Bound radioactivity was quantified by scintillation proximity spectroscopy using the Topcount (Packard Bio-Science Co., Meriden, Conn.).

The amount of cAMP produced per mL of reaction was extrapolated from the cAMP standard curve, according to the instructions provided in the manufacturer's user manual. Data were analyzed by nonlinear regression analysis with the GraphPad Prism Software package using the 3-parameter sigmoidal dose-response model (slope constrained to unity). Potency data are reported as $pEC_{50}$ values, the negative decadic logarithm of the $EC_{50}$ value, where $EC_{50}$ is the effective concentration for a 50% maximal response.

Test compounds exhibiting a higher $pEC_{50}$ value in this assay have a higher potency for agonizing the 5-HT$_4$ receptor. The compound of the invention which was tested in this assay, for example, in the cell line (1) having a density of about 0.5-0.6 pmol/mg protein, had a $pEC_{50}$ value above about 9.

Assay 4: In vitro Voltage Clamp Assay of Inhibition of Potassium Ion Current in Whole Cells Expressing the hERG Cardiac Potassium Channel CHO-K1 cells stably transfected with hERG cDNA were obtained from Gail Robertson at the University of Wisconsin. Cells were held in cryogenic storage until needed. Cells were expanded and passaged in Dulbecco's Modified Eagles Medium/F12 supplemented with 10% fetal bovine serum and 200 µg/mL geneticin. Cells were seeded onto poly-D-lysine (100 µg/mL) coated glass coverslips, in 35 mm$^2$ dishes (containing 2 mL medium) at a density that enabled isolated cells to be selected for whole cell voltage-clamp studies. The dishes were maintained in a humidified, 5% CO$_2$ environment at 37° C.

Extracellular solution was prepared at least every 7 days and stored at 4° C. when not in use. The extracellular solution contained (mM): NaCl (137), KCl (4), CaCl$_2$ (1.8), MgCl$_2$ (1), Glucose (10), 4-(2-hydroxyethyl)-1-piperazineethane-sulphonic acid (HEPES) (10), pH 7.4 with NaOH. The extracellular solution, in the absence or presence of test compound, was contained in reservoirs, from which it flowed into the recording chamber at approximately 0.5 mL/min. The intracellular solution was prepared, aliquoted and stored at –20° C. until the day of use. The intracellular solution contained (mM): KCl (130), MgCl$_2$ (1), ethylene glycol-bis(beta-aminoethyl ether) N,N,N',N'-tetra acetic acid salt (EGTA) (5), MgATP (5), 4-(2-hydroxyethyl)-1-piperazineethanesulphonic acid (HEPES) (10), pH 7.2 with KOH. All experiments were performed at room temperature (20-22° C.).

The coverslips on which the cells were seeded were transferred to a recording chamber and perfused continuously. Gigaohm seals were formed between the cell and the patch electrode. Once a stable patch was achieved, recording commenced in the voltage clamp mode, with the initial holding potential at –80 mV. After a stable whole-cell current was achieved, the cells were exposed to test compound. The standard voltage protocol was: step from the holding potential of –80 mV to +20 mV for 4.8 sec, repolarize to –50 mV for 5 sec and then return to the original holding potential (–80 mV). This voltage protocol was run once every 15 sec (0.067 Hz). Peak current amplitudes during the repolarization phase were determined using pClamp software. Test compounds at a concentration of 3 µM were perfused over the cells for 5 minutes, followed by a 5-minute washout period in the absence of compound. Finally a positive control (cisapride, 20 nM) was added to the perfusate to test the function of the cell. The step from –80 mV to +20 mV activates the hERG channel, resulting in an outward current. The step back to –50 mV results in an outward tail current, as the channel recovers from inactivation and deactivates.

Peak current amplitudes during the repolarization phase were determined using pCLAMP software. The control and test article data were exported to Origin® (OriginLab Corp., Northampton Mass.) where the individual current amplitudes were normalized to the initial current amplitude in the absence of compound. The normalized current means and standard errors for each condition were calculated and plotted versus the time course of the experiment.

Comparisons were made between the observed K$^+$ current inhibitions after the five-minute exposure to either the test article or vehicle control (usually 0.3% DMSO). Statistical comparisons between experimental groups were performed using a two-population, independent t-test (Microcal Origin v. 6.0). Differences were considered significant at $p<0.05$.

The smaller the percentage inhibition of the potassium ion current in this assay, the smaller the potential for test compounds to change the pattern of cardiac repolarization when used as therapeutic agents. The compound of the invention which was tested in this assay at a concentration of 3 µM exhibited an inhibition of the potassium ion current of less than about 20%.

Assay 5: In vitro Model of Oral Bioavailability: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

Caco-2 (colon, adenocarcinoma; human) cells were obtained from ATCC (American Type Culture Collection; Rockville, Md.). For the permeation study, cells were seeded at a density of 63,000 cells/cm$^2$ on pre-wetted transwells polycarbonate filters (Costar; Cambridge, Mass.). A cell monolayer was formed after 21 days in culture. Following cell culture in the transwell plate, the membrane containing the cell monolayer was detached from the transwell plate and inserted into the diffusion chamber (Costar; Cambridge, Mass.). The diffusion chamber was inserted into the heating block which was equipped with circulating external, thermostatically regulated 37° C. water for temperature control. The air manifold delivered 95% $O_2$/5% $CO_2$ to each half of a diffusion chamber and created a laminar flow pattern across the cell monolayer, which was effective in reducing the unstirred boundary layer.

The permeation study was performed with test compound concentrations at 100 μM and with $^{14}$C-mannitol to monitor the integrity of the monolayer. All experiments were conducted at 37° C. for 60 min. Samples were taken at 0, 30 and 60 min from both the donor and receiver sides of the chamber. Samples were analyzed by HPLC or liquid scintillation counting for test compound and mannitol concentrations. The permeation coefficient ($K_p$) in cm/sec was calculated.

In this assay, a $K_p$ value greater than about $10 \times 10^{-6}$ cm/sec is considered indicative of favorable bioavailability. The compound of the invention exhibited a $K_p$ value greater than about $50 \times 10^{-6}$ cm/sec.

Assay 6: Pharmacokinetic Study in the Rat

Aqueous solution formulations of test compounds were prepared in 0.1% lactic acid at a pH of between about 5 and about 6. Male Sprague-Dawley rats (CD strain, Charles River Laboratories, Wilmington, Mass.) were dosed with test compounds via intravenous administration (IV) at a dose of 2.5 mg/kg or by oral gavage (PO) at a dose of 5 mg/kg. The dosing volume was 1 mL/kg for IV and 2 mL/kg for PO administration. Serial blood samples were collected from animals pre-dose, and at 2 (IV only), 5, 15, and 30 min, and at 1, 2, 4, 8, and 24 hours post-dose. Concentrations of test compounds in blood plasma were determined by liquid chromatography-mass spectrometry analysis (LC-MS/MS) (MDS SCIEX, API 4000, Applied Biosystems, Foster City, Calif.) with a lower limit of quantitation of 1 ng/mL.

Standard pharmacokinetic parameters were assessed by non-compartmental analysis (Model 201 for IV and Model 200 for PO) using WinNonlin (Version 4.0.1, Pharsight, Mountain View, Calif.). The maximum in the curve of test compound concentration in blood plasma vs. time is denoted $C_{max}$. The area under the concentration vs. time curve from the time of dosing to the last measurable concentration (AUC (0-t)) was calculated by the linear trapezoidal rule. Oral bioavailability (F (%)), i.e. the dose-normalized ratio of AUC(0-t) for PO administration to AUC(0-t) for IV administration, was calculated as:

$$F (\%) = AUC_{PO}/AUC_{IV} \times Dose_{IV}/Dose_{PO} \times 100\%$$

Test compounds which exhibit larger values of the parameters $C_{max}$, AUC(0-t), and F (%) in this assay are expected to have greater bioavailability when administered orally. The compound of the invention had a $C_{max}$ value of 0.8 μg/mL, an AUC(0-t) value of 1.2 μg·hr/mL and oral bioavailability (F (%)) in the rat model of about 75%.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A pharmaceutical composition comprising a therapeutically effective amount of a crystalline compound, wherein the crystalline compound is crystalline 4-(4-{[(2-isopropyl-1H-benzoimidazole-4-carbonyl)-amino]methyl}piperidin-1-yl-methyl)piperidine-1-carboxylic acid methyl ester or a monohydrate thereof, and a pharmaceutically acceptable carrier.

2. A method of treating a mammal having a medical condition selected from irritable bowel syndrome, chronic constipation, functional dyspepsia, delayed gastric emptying, gastroesophageal reflux disease, gastroparesis, post-operative ileus, intestinal pseudo-obstruction, and drug-induced delayed transit, the method comprising administering to the mammal, a therapeutically effective amount of a pharmaceutical composition comprising a pharmaceutically-acceptable carrier and a crystalline compound, wherein the crystalline compound is crystalline 4-(4-{[2-isopropyl-1H-benzoimida-zole-4-carbonyl)-amino]methyl}piperidin-1-ylmethyl)piperidine-1-carboxylic acid methyl ester or a monohydrate thereof.

3. A method of treating a disorder of reduced motility of the gastrointestinal tract in a mammal, the method comprising administering to the mammal, a therapeutically effective amount of a pharmaceutical composition comprising a pharmaceutically-acceptable carrier and a crystalline compound, wherein the crystalline compound is crystalline 4-(4-{[(2-isopropyl-1H-benzoimidazole-4-carbonyl) -amino]methyl}piperidin-1-ylmethyl)piperidine-1-carboxylic acid methyl ester or a monohydrate thereof.

4. The method of claim 3, wherein the disorder of reduced motility is selected from chronic constipation, constipation-predominant irritable bowel syndrome, diabetic and idiopathic gastroparesis, and functional dyspepsia.

5. The pharmaceutical composition of claim 1 wherein the crystalline compound is crystalline 4-(4-{[(2-isopropyl-1H-benzoimidazole-4-carbonyl) -amino]methyl}piperidin-1-yl-methyl)piperidine-1-carboxylic acid methyl ester.

6. The pharmaceutical composition of claim 5 wherein the crystalline compound is characterized by a powder x-ray diffraction pattern having two or more diffraction peaks at 2θ values selected from 15.08±0.10, 15.41±0.10, 19.00±0.10, 19.70±0.10, and 23.68±0.10.

7. The pharmaceutical composition of claim 5 wherein the crystalline compound is characterized by a differential scanning calorimetry profile which shows a maximum in endothermic heat flow at a temperature in the range of about 146° C. to about 148° C.

8. The pharmaceutical composition of claim 1 wherein the crystalline compound is crystalline 4-(4-{[(2-isopropyl-1H-benzoimidazole-4-carbonyl)-amino]methyl}piperidin-1-yl-methyl)piperidine-1-carboxylic acid methyl ester monohydrate.

9. The method of claim 2 wherein the crystalline compound is crystalline 4-(4-{[(2-isopropyl-1H-benzoimidazole-4-carbonyl)-amino]methyl}piperidin-1-ylmethyl)piperidine-1-carboxylic acid methyl ester.

10. The method of claim 2 wherein the crystalline compound is crystalline 4-(4-{[(2-isopropyl-1H-benzoimidazole-4-carbonyl)-amino]methyl}piperidin-1-ylmethyl)piperidine-1-carboxylic acid methyl ester monohydrate.

11. The method of claim 3 wherein the crystalline compound is crystalline 4-(4-{[(2-isopropyl-1H-benzoimidazole-4-carbonyl)-amino]methyl}piperidin-1-ylmethyl)piperidine-1-carboxylic acid methyl ester.

12. The method of claim 3 wherein the crystalline compound is crystalline 4-(4-{[(2-isopropyl-1H-benzoimidazole-4-carbonyl)-amino]methyl}piperidin-1-ylmethyl)piperidine-1-carboxylic acid methyl ester monohydrate.

13. The method of claim 4 wherein the crystalline compound is crystalline 4-(4-{[(2-isopropyl-1H-benzoimidazole-4-carbonyl)-amino]methyl}piperidin-1-ylmethyl)piperidine-1-carboxylic acid methyl ester.

14. The method of claim 13 wherein the crystalline compound is characterized by a powder x-ray diffraction pattern having two or more diffraction peaks at 2θ values selected from 15.08±0.10, 15.41±0.10, 19.00±0.10, 19.70±0.10, and 23.68±0.10.

15. The method of claim 13 wherein the crystalline compound is characterized by a differential scanning calorimetry profile which shows a maximum in endothermic heat flow at a temperature in the range of about 146° C. to about 148° C.

16. The method of claim 4 wherein the crystalline compound is crystalline 4-(4-{[(2-isopropyl-1H-benzoimidazole-4-carbonyl)-amino]methyl}piperidin-1-ylmethyl)piperidine-1-carboxylic acid methyl ester monohydrate.

17. The method of claim 16 wherein the crystalline compound is characterized by a powder x-ray diffraction pattern having two or more diffraction peaks at 2θ values selected from 9.14±0.20, 12.41±0.20, 12.74±0.20, 17.75±0.20, 18.47±0.20, 20.63±0.20, 21.13±0.20, and 27.05±0.20.

18. The pharmaceutical composition of claim 8 wherein the crystalline compound is characterized by a powder x-ray diffraction pattern having two or more diffraction peaks at 2θ values selected from 9.14±0.20, 12.41±0.20, 12.74±0.20, 17.75±0.20, 18.47±0.20, 20.63±0.20, 21.13±0.20, and 27.05±0.20.

* * * * *

UNITED STATES PATENT AND TRADEMARK OFFICE
CERTIFICATE OF CORRECTION

PATENT NO. : 7,622,587 B2  Page 1 of 1
APPLICATION NO. : 11/807664
DATED : November 24, 2009
INVENTOR(S) : Dalziel et al.

It is certified that error appears in the above-identified patent and that said Letters Patent is hereby corrected as shown below:

On the Title page (section (62))
line 29, "7,256,394" should be "7,256,294".

Signed and Sealed this

Sixteenth Day of February, 2010

David J. Kappos
*Director of the United States Patent and Trademark Office*